United States Patent
Ralfs

(10) Patent No.: US 11,925,757 B2
(45) Date of Patent: Mar. 12, 2024

(54) VENTILATOR

(71) Applicant: Drägerwerk AG & Co. KGaA, Lübeck (DE)

(72) Inventor: Frank Ralfs, Lübeck (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 377 days.

(21) Appl. No.: 17/191,931

(22) Filed: Mar. 4, 2021

(65) Prior Publication Data

US 2021/0275764 A1  Sep. 9, 2021

(30) Foreign Application Priority Data

Mar. 6, 2020 (DE) ..................... 10 2020 001 440.2

(51) Int. Cl.
*A61M 16/00* (2006.01)
*A61M 16/04* (2006.01)
(Continued)

(52) U.S. Cl.
CPC ........ *A61M 16/024* (2017.08); *A61M 16/204* (2014.02); *A61M 16/205* (2014.02);
(Continued)

(58) Field of Classification Search
CPC ............ A61M 16/0057; A61M 16/024; A61M 16/026; A61M 16/204; A61M 2230/30;
(Continued)

(56) References Cited

U.S. PATENT DOCUMENTS 5,769,082 A * 6/1998 Perel ..................... A61B 5/029
600/484
6,345,619 B1    2/2002 Finn
(Continued)

FOREIGN PATENT DOCUMENTS

CN   105899249 A   8/2016
DE   69710100 T2   7/2002
(Continued)

OTHER PUBLICATIONS

Assessing Fluid-Responsiveness by a Standardized Ventilatory Maneuver: The Respiratory Systolic Variation Test. Anesthesia & Analgesia 100(4):p. 942-945, Apr. 2005 (Year: 2005).*
(Continued)

*Primary Examiner* — Kendra D Carter
*Assistant Examiner* — Mautin I Ashimiu
(74) *Attorney, Agent, or Firm* — McGlew and Tuttle, P.C.

(57) ABSTRACT

A ventilator (1) with a control unit (49). The control unit (49) controls the inhalation valve (41) and the exhalation valve (43) in order to raise an inhalation pressure level from a first pressure level to a predefined second pressure level and to maintain the inhalation pressure level for a first predefined time period and the control unit (49) controls the inhalation valve (41) and the exhalation valve (43) to raise the second pressure level to a predefined third pressure level and to maintain the third pressure level for a second predefined time period. The control unit (49) takes into consideration predefined values (80) for controlling the pressure levels and for controlling the time periods.

24 Claims, 6 Drawing Sheets

(51) Int. Cl.
*A61M 16/06* (2006.01)
*A61M 16/08* (2006.01)
*A61M 16/20* (2006.01)

(52) U.S. Cl.
CPC ..... *A61M 2016/0027* (2013.01); *A61M 16/04* (2013.01); *A61M 16/0465* (2013.01); *A61M 16/06* (2013.01); *A61M 16/0833* (2014.02); *A61M 2230/30* (2013.01)

(58) Field of Classification Search
CPC ........... A61M 2016/0027; A61M 16/202–205; A61M 2230/46
See application file for complete search history.

(56) References Cited

U.S. PATENT DOCUMENTS

| | | | |
|---|---|---|---|
| 2008/0243016 | A1 | 10/2008 | Liao et al. |
| 2009/0120439 | A1 | 5/2009 | Goebel |
| 2019/0231202 | A1 | 8/2019 | Kremeier |
| 2019/0371460 | A1* | 12/2019 | Gutierrez ............ A61M 16/026 |
| 2020/0282163 | A1* | 9/2020 | Schranz ............. A61M 16/205 |
| 2021/0038840 | A1* | 2/2021 | Oddo ................ A61M 16/0063 |
| 2021/0361964 | A1* | 11/2021 | Pargger .................. A61N 2/002 |
| 2022/0218928 | A1* | 7/2022 | Liu ..................... A61M 16/024 |

FOREIGN PATENT DOCUMENTS

| | | |
|---|---|---|
| DE | 102012024672 A1 | 6/2014 |
| DE | 102007062214 C5 | 12/2017 |
| DE | 102017217858 A1 | 4/2019 |
| DE | 102018003026 A1 | 10/2019 |
| EP | 1972274 A1 | 9/2008 |
| EP | 2923641 A1 | 9/2015 |
| EP | 3520850 A1 | 8/2019 |
| GB | 2455844 A | 6/2009 |
| WO | 9812965 A1 | 4/1998 |
| WO | 2019068496 A1 | 4/2019 |

OTHER PUBLICATIONS

Comparison of an automated respiratory systolic variation test with dynamic preload indicators to predict fluid responsiveness after major surgery, BJA: British Journal of Anaesthesia, vol. 111, Issue 5, Nov. 2013, pp. 736-742 (Year: 2013).*

* cited by examiner

VENTILATOR

CROSS REFERENCE TO RELATED APPLICATIONS

This application claims the benefit of priority under 35 U.S.C. § 119 of German Application 10 2020 001 440.2, filed Mar. 6, 2020, the entire contents of which are incorporated herein by reference.

TECHNICAL FIELD

The present invention pertains to a ventilator for a mechanical ventilation of patient for use in a combination with a physiological patient monitor. The combined use of the ventilator with the physiological patient monitor forms a system comprising a ventilator and a physiological patient monitor. A status of the cardiovascular system of a patient can be diagnosed by means of a patient monitor. The patient monitor is capable of carrying out invasive or non-invasive blood pressure measurements, temperature measurement, EKG measurements and measurements of the oxygen saturation at the patient. Ventilators are used to supply the patient with breathing gases. The status of the cardiovascular system is influenced by both the liquid balance of the patient and his medication. The present invention makes it possible by the combination of the ventilator with the patient monitor to obtain an estimate on whether additional liquid should be administered to the patient or whether the administration of additional liquid is rather detrimental for the therapeutic goal and other actions should be taken into consideration to stabilize the circulation. Such a test is also called "Respiratory Systolic Variation Test" (RSVT). The term "RSVT maneuver" is also commonly used to designate the performance of the test by a ventilator. This test is usually carried out in such a manner that the ventilation pressure is increased by the ventilator in stages. An arterial blood pressure measurement is then carried out at the same time by the patient monitor at these pressure stages of the ventilation pressure.

TECHNICAL BACKGROUND

This maneuver is usually carried out as a standardized maneuver with steps of the ventilation pressure during consecutive phases of inhalation from a given or set pressure level of, for example, 10 cmH$_2$O with pressure increases from 10 cmH$_2$O to 20 cmH$_2$O and then to 30 cmH$_2$O relative to the pressure level given or set at the start of the maneuver. Indicating ventilation pressures in the unit cmH$_2$O instead of an indication in SI units in hPa or often also in mbar is common in the field of medicine and it shall also be maintained therefore for the sake of clarity within the framework of the present invention. A response, which is seen in the measured arterial blood pressure, is, for example, such that the minima of the ventilation-induced arterial blood pressure fluctuations measured by the monitor drop from a previous value above 120 mmHg at first to 100 mmHg and finally to 80 mmHg. A slope value Slope$_{RSVT}$ from 40 mmHg to 20 cmH$_2$O, i.e., a value with an absolute value of 20 is obtained from these differences. This slope value Slopes$_{RSVT}$ with an absolute value of 20 can then be used to estimate whether the state of the patient would be improved by the administration of additional liquid. This slope value of 20, calculated as an example, is above a typical threshold of 15, which characterizes a type of patient whose health status would improve on administration of liquid. Such a patient would be a so-called "fluid responder," i.e., the patient would respond with an increase in the cardiac minute volume following the administration of liquid.

In the standardized, usual embodiment as a maneuver with a stepwise pressure increase of the ventilator during the inhalation, this RSVT maneuver does, however, have the disadvantages that individual peculiarities of the individual patient concerning the properties of his lungs, thorax and abdominal cavity do affect the determination of the slope, which can then affect the decision to take appropriate measures, for example, the administration of additional liquid.

Disadvantageous is, in particular, the situation that differences in the elasticity of the lungs and of the respiratory system, comprising the lungs and the thorax, may lead to different calculations of the slope in different patients and an otherwise identical cardiovascular situation.

Processes for determining properties of the lungs and of the respiratory system, comprising the lungs and the thorax, as well as of the entire respiratory system of a patient are known from the state of the art. Measurement-based processes based on the use of measurement maneuvers are used for this purpose, which can be carried out by a ventilator. For example, a process involving the analysis of different pulmonary states in different situations in the course of the ventilation may be used.

A process of this type with analysis of a change in an end-expiratory lung volume (change in end-expiratory lung volume, ΔEELV) is described in EP 2923641 A1.

Another possibility of determining pulmonary properties can be carried out by suitable maneuvers with short-term blockage of the flow of breathing gases into the lungs and/or out of the lungs by means of so-called occlusion. Changes as well as pressure and flow rate compensation processes are provoked here by the occlusions, whose time characteristics can then be analyzed to derive therefrom properties of the lungs and of the respiratory system comprising the lungs and the thorax. EP 1972274 A1 describes an occlusion maneuver of this type.

EP 3520850 A1 and US 2009 0120439 A1 describe how the control of a mechanical ventilation can be carried out by means of a pressure sensor arranged in the esophagus within the thoracic cavity of the patient.

It can be determined by measurement by means of such an esophageal pressure sensor how the inspiratory ventilation pressure applied by the ventilation is distributed currently during the mandatory ventilation in the respiratory system (lungs, thorax) as a ventilation pressure acting in the alveoli of the lungs and as a pressure effect on the heart and on the ability to function (cardiac output, heart rate) of the myocardium.

This distribution of the ventilation pressure depends on the ratio of the elasticity or stiffness of the lungs (lung elastance) to the elasticity of the respiratory system comprising the lungs and the thorax (overall elastance) and it is influenced, among other things, by the clinical picture and the body weight of the patient.

The ventilation pressure is distributed nearly uniformly in a typical patient with healthy lungs and normal body weight, i.e., the pressure distribution in percentage between the lungs and the heart ranges from 40% to 60% to 60% to 40%. The ventilation pressure has, for example, an uneven distribution in a patient with an acute respiratory distress syndrome (ARDS). A state of a so-called "stiff lungs" is seen in this example, which can be assigned as a property (diagnosis) individually to individual patients, to special types of patients and may, moreover, also be stored as property data for being available in data banks as well as in patient data management systems.

SUMMARY

An object of the present invention is to propose a ventilator, which makes it possible to carry out an RSVT maneuver individualized for an individual patient with individualized ventilation pressure levels of the inspiratory ventilation pressure $P_{insp}$ for the purpose of a standardized and hence comparable stimulus for predicting the volume responsiveness.

Another object of the present invention is to provide a system with a ventilator and with a measuring device suitable for blood pressure measurement for carrying out an RSVT maneuver in an individualized manner.

According to a first aspect of the present invention, a ventilator is configured such that a maneuver with at least two inspiratory ventilation pressure levels can be applied. This embodiment according to the present invention is configured by a ventilator for a mechanical ventilation of a patient. The ventilator has an exhalation valve, an inhalation valve, an inhalation pressure sensor, an exhalation pressure sensor, a control unit as well as a data interface for providing predefined values for the control unit. The data interface may be configured as a part of a data input unit as a component of the control unit or it may form an independent unit in the system. Furthermore, the ventilator has a connection system with an inhalation line for feeding breathing gases to the patient and with an exhalation line for removing breathing gases from the patient. The connection system has, furthermore, a connection element for connecting the inhalation line and the exhalation line directly close to the patient. This connection element is preferably configured as a so-called Y-piece. In a variant with a so-called single-tube system, the exhalation line with the exhalation valve is arranged in the connection element directly close to the patient, so that breathing gases are removed to the environment directly close to the patient, without passing them on to the ventilator.

The inhalation pressure sensor is arranged in or at the inhalation line of the connection system. The inhalation pressure sensor is configured for detecting an inhalation pressure measured value and for providing the inhalation pressure measured value for the control unit. The exhalation pressure sensor is arranged in or at the expiratory discharge line of the connection system. The exhalation pressure sensor is configured for detecting an exhalation pressure measured value and for providing the exhalation pressure measured value for the control unit.

The control unit is configured to control the inhalation valve by taking into consideration the inhalation pressure measured value in order to provide an inhalation pressure level via the inhalation line of the connection system for the patient. The control unit is further configured to control the exhalation valve by taking into consideration the exhalation pressure measured value in order to provide an exhalation pressure level for the patient via the exhalation line of the connection system.

The control unit is configured according to the present invention to carry out a controlled maneuver with a sequence of increases in the inhalation pressure level. The maneuver is carried out such that the control unit is configured to control the inhalation valve and the exhalation valve such as to raise the inhalation pressure level p from a first pressure level to a predefined second pressure level and to maintain it for a predefined time period and subsequently to control the inhalation valve and the exhalation valve such as to raise the second pressure level to a predefined third pressure level and to maintain the third pressure level for a second predefined time period. The control unit is further configured to take predefined values into consideration during the control of the pressure levels and during the control of the time periods.

A two-step pressure increase makes it possible to begin and end the RSVT maneuver within a phase of inhalation, so that the effect on the blood pressure can be determined for the duration of only one phase of inhalation. The increases in the inhalation pressure $P_{insp}$ may also be applied, as an alternative, distributed over a sequence of two or more phases of inhalation.

In a preferred embodiment of the ventilator, the control unit is configured to control the inhalation valve and the exhalation valve such as to raise the third pressure level to a predefined fourth pressure level and to maintain it for a third predefined time period. This embodiment of the ventilator with the control unit with three or more pressure stages offers, for example, the following advantages, namely, that the effect of the increase in the inhalation pressure $P_{insp}$ on the blood pressure can be carried out, on the one hand, in a more significant manner as well as also in finer steps. A three-step pressure increase makes it optionally possible, depending on the setting of the ventilation rate, to begin and to end the maneuver within a phase of inhalation, so that the effect on the blood pressure can be determined immediately for the duration of only one phase of inhalation. The three-step pressure increase may, however, be applied just as well over a sequence of three phases of inhalation or over a plurality of phases of inhalation. A distribution among a plurality of phases of inhalation makes it possible to take into account different time constants of different patients or patient types in reference to the response and to the change in the blood pressure during the determination of the inhalation pressure $P_{insp}$.

In a preferred embodiment of the ventilator, the predefined values comprise predefined values for raising the inhalation pressure level $P_{insp}$ from the first pressure level to the second pressure level and for raising to the third pressure level. This preferred embodiment of the ventilator offers, for example, the following advantages in the embodiment of the individual embodiment of the pressure level. If the usual first pressure level, which is not adapted individually specifically to one patient or patient type, is predefined, for example, as a pressure increase of 10 cmH$_2$O for a standard RSVT maneuver, a pressure increase by, for example, 12 cmH$_2$O to the second pressure level and then another increase by, for example, 11 cmH$_2$O to the third pressure level can be brought about by the control unit specifically and individually, depending on the properties of the lungs of the individual patient and/or depending on the clinical picture or patient type, from a starting pressure level of the inspiratory ventilation pressure $P_{insp}$ of the ventilation being currently carried out. If measured values of the systolic blood pressure are detected by the measuring device chronologically largely synchronously at the time of setting the second and third pressure levels, an analysis can be carried out concerning the volume responsiveness of the patient from the pressure difference between the three pressure levels of the ventilation pressure, in this example 12 cmH$_2$O and 11 cmH$_2$O, with the blood pressure measured values determined for this. The control unit can relate a mean change in the blood pressure from the measured value at the beginning of the RSVT maneuver until the measured value that was detected synchronously in time with the third pressure level to the mean change in the inspiratory ventilation pressure $P_{insp}$, 11.5 cmH$_2$O in this example, in order to carry out the analysis concerning the volume responsiveness of the patient; as an alternative, the control unit can relate for the individual pressure levels the respective changes in the measured values of the blood pressure to the respective individual pressure levels and then possibly carry out suitable averagings based on this.

In a preferred embodiment of the ventilator, the predefined values comprise predefined values for raising the inhalation pressure level $P_{insp}$ for a raise from the third pressure level to the fourth pressure level. For example, the control unit would carry out a pressure increase from an initial pressure level of the inspiratory ventilation pressure $P_{insp}$ of the ventilation being currently carried out by, for example, 12 cmH$_2$O to the second pressure level and then another increase by, for example, 11 cmH$_2$O to the third pressure level and then another increase by, for example, 10 cmH$_2$O to the fourth pressure level as an individualized RSVT maneuver. This preferred embodiment of the ventilator offers the advantage that the control unit can carry out for the analysis of the volume responsiveness of the patient on the basis of three detected blood pressure measured values of the patient and, corresponding to these, on the basis of essentially three corresponding blood pressure measured values that are essentially synchronous in time.

The control unit can relate a mean change in the blood pressure from the measured value at the beginning of the RSVT maneuver until the measured value that was detected synchronously in time with the fourth pressure level to the mean change in the inspiratory ventilation pressure $P_{insp}$ in order to carry out the analysis concerning the volume responsiveness of the patient; as an alternative, the control unit can relate for the individual pressure levels the respective changes in the measured values of the blood pressure to the respective individual pressure levels and then possibly carry out suitable averagings based on this.

This increase in the support values available for the analysis to three blood pressure measured values offers the possibility that possible incorrect measurements become detectable in the blood pressure measured value in a simple manner when the analysis is carried out by the control unit.

Further increases in the pressure levels would be advantageous, for example, from the viewpoint of an increased reliability of the measurement, but the well-being of the patient must be taken into consideration when the maneuver is being carried out, and frequent and/or marked excessive increases of the ventilation pressure should therefore be avoided as much as possible when RSVT maneuvers are being carried out.

A three-step pressure increase according to this preferred embodiment thus represents a balanced compromise between requirements imposed in terms of measurement and the burden for the patient and it is therefore also established in this form in clinical practice. The patient type may comprise, on the one hand, characteristics such as height, body weight, sex, age; in addition, special clinical pictures of the lungs or cardiovascular system may be typified as well. This makes possible both an individual and, moreover, typified variation of the pressure stages during the performance of the RSVT maneuver. Chronic obstructive pulmonary disease (COPD) or pulmonary or extrapulmonary restrictive pulmonary diseases shall be mentioned here as pulmonary diseases as an example.

In another preferred embodiment of the ventilator, the predefined values comprise the time periods for maintaining the second and third pressure levels.

In a preferred embodiment of the ventilator, the predefined values comprise the time periods for maintaining the fourth pressure level. Inclusion of the time periods for maintaining the pressure levels leads to the advantage of a further individualization of the RSVT maneuver. It thus becomes possible to include both aspects of the ventilation control, for example, set values of the ventilation rate and time periods of the phase of inhalation and of the phase of exhalation, and aspects of the blood pressure measurement, for example, the heart rate of the patient in the configuration of the RSVT maneuver such that the ventilation by the ventilator and also the physiological monitoring by the measuring device must be interrupted or only interfered with in a manner essentially noticeable for the patient. The possibility of configuring variable time periods for maintaining the pressure levels makes possible in a special manner a good synchronization in time and/or an adaptation of the RSVT maneuver with the state of the patient, the patient type, the clinical picture and the current situations of the patient, the ventilation of the patient as well as the monitoring of the patient by the measuring device.

In other preferred embodiments, the ventilator may have an additional pressure sensor. The additional pressure sensor is configured to detect current measured values, which indicate a pressure situation inside the patient. The additional pressure sensor is configured for indirectly and/or directly providing the measured value, which indicates the pressure situation inside the patient, for the control unit. In these additional preferred embodiments, which are equipped with an additional pressure sensor, the control unit is configured, for example, to determine the predefined values on the basis of measured values of the additional pressure sensor and/or of measured values of the inhalation pressure sensor or of the exhalation pressure sensor, wherein the inhalation pressure sensor is suitable for determining the predefined values during the phase of inhalation of the ventilation and wherein the exhalation pressure sensor is suitable for determining the predefined values during the phase of exhalation of the ventilation.

The additional pressure sensor is arranged in the preferred embodiments as a pressure sensor located close to the patient in the vicinity of the patient or at the esophagus of the patient. This so-called esophageal pressure sensor is inserted into the esophagus of the patient and it makes possible an esophageal pressure measurement (esophageal manometry) and it depicts the effects of the applied inspiratory ventilation pressure on the region between the lungs and the thorax by measurement.

In an especially preferred variant of these embodiments, the control unit is configured to take into consideration the measured value, which indicates an airway pressure ($P_{AW}$) of the patient, together with the measured value of the additional pressure sensor, especially of the esophageal pressure sensor. Using the measured values of the esophageal pressure sensor and the measured values that indicate an airway pressure ($P_{AW}$) of the patient, the control unit is able to distinguish the effect of the ventilation on the lungs from the effect of the ventilation on other body parts and tissues in the area of the thorax (ribs, costal muscles, respiratory muscles, myocardium). The esophageal pressure sensor thus depicts in the subtraction of the airway pressure ($P_{AW}$) the effects of the applied inspiratory ventilation pressure applied on the lungs, but not on all other regions of the thorax, by measurement. It is thus made possible to determine the portion of the ventilation pressure that acts on the lungs due to the subtraction of the measured values of the esophageal pressure sensor from the measured values that indicate the airway pressure ($P_{AW}$) of the patient. The portion of the ventilation pressure remaining after the subtraction can then be assigned in terms of the effect indirectly to the heart and some portions of this remaining portion can also be assigned to the thorax. Depending on the phase of ventilation, both the inhalation pressure sensor and the exhalation pressure sensor are suitable for determining measured values that indicate airway pressures ($P_{AW}$) of the patient. When the RSVT maneuver is applied during phases of inhalation of the ventilation, the measured value ($P_{insp}$) of the inhalation pressure sensor is used for the subtraction, just like for the determination by measurement of the first, second, third and even fourth pressure level. The esophageal pressure sensor makes it thus possible in an especially advantageous manner, when used with the RSVT maneuver, to determine the individual distribution of the ventilation pressure, which distribution is typical for a defined patient, based on the individual ratio of the elasticity or stiffness of the lungs (lung elastance) to the elasticity of the respiratory system comprising the lungs and the thorax (overall elastance). In the knowledge of the distribution of the pressures administered on the lungs and on the thorax, the pressure acting on the heart can be determined and then applied, in a correspondingly adapted manner, with an RSVT maneuver. In particular, the effect of the ventilation pressures applied and the effect of changes in the ventilation pressures applied on the heart, which are elicited by the RSVT maneuver, can thus be advantageously determined. The ventilation pressures applied act as a stimulus on the cardiovascular system and become noticeable as a system response in changes of the blood pressure. Diagnostic hypotheses can be derived from these changes in the blood pressure concerning certain properties, e.g., concerning the volume responsiveness (fluid response) of the patient. The stimulus underlying this system response with individualized pressure stages of the ventilation pressure is thus more standardized and more comparable compared to a use of the RSVT maneuver without individualized pressure stages. The information arising concerning the volume responsiveness is, on the whole, more reliable; moreover, needlessly high overall pressures can be avoided, which also helps avoid needless burdens for the patient. Thus, the acceptance of the RSVT maneuver increases in clinical practice due to the possibility of administering lower ventilation pressures.

In other preferred embodiments of the ventilator, the control unit is configured to determine or to estimate the predefined values on the basis of values established or determined chronologically before or on the basis of provided values, which indicate individual stiffnesses or elasticities of the lungs, thorax and/or of the respiratory system of the patient. A possibility of obtaining values that indicate individual stiffnesses or elasticities of the lungs, thorax and/or of the respiratory system of the patient arises by means of a determination of the values which is carried out chronologically before the performance of the RSVT maneuver. A determination of the values that indicate individual stiffnesses or elasticities of the lungs, thorax and/or of the respiratory system of the patient can be carried out, for example, by means of the esophageal pressure sensor, or it may have been carried out chronologically before this. To determine predefined values and to use them in the RSVT maneuver, it is possible to use, during the application and especially during the repeated application of the RSVT maneuver, measured values determined before simultaneously during a previously performed RSVT maneuver with the esophageal pressure sensor or values derived from these measured values, which indicate individual stiffnesses or elasticities of the lungs, thorax and/or of the respiratory system of the patient. The esophageal pressure sensor is thus used in such an embodiment for the initial individual characterization of the properties of the lungs and/or of the thorax of a patient and need not therefore be applied any longer over the long term in the esophagus within the framework of monitorings carried out following this chronologically with the performance of additional RSVT maneuvers. This functionality of the additional pressure sensor, especially of the esophageal pressure sensor, leads for the control unit in this preferred embodiment, for example, to the following possibilities and advantages that the estimation of the individual stiffnesses or elasticities of the lungs, thorax and/or of the respiratory system of the patient reflect the real state, i.e., the real, currently given pressure ratios in the lungs of the patient. The additional pressure sensor makes it possible for the control unit continuously to monitor the pressure level set and brought about in the lungs by the inhalation pressure $P_{insp}$ and to select the preset values for the increases in the inhalation pressure $P_{insp}$ in a suitable manner and to select the increases in the inhalation pressure $P_{insp}$, such that the pressure level set is not increased needlessly in the alveoli during these increases in the inhalation pressure $P_{insp}$ and a sufficiently significant effect is nevertheless achieved in the change in the blood pressure in order to obtain, for example, the information on whether the patient in question belongs to the group of the "fluid responders." The pressure level that is effective and necessary for the prediction of the volume responsiveness can thus be determined more accurately and it may therefore also turn out to be lower than it would be if the conditions were unknown.

The control unit may be configured in preferred embodiments of the ventilator to carry out the determination or estimation of the predefined values on the basis of provided property values of patients. In a preferred embodiment of the ventilator, the control unit is configured to determine or to estimate the predefined values on the basis of an individually determined ratio of the stiffness or elasticity of the lungs to the stiffness of elasticity of the respiratory system comprising the lungs and the thorax. Individually determined ratios of the stiffness or elasticity of the lungs to the stiffness or elasticity of the respiratory system comprising the lungs and thorax can be obtained by the control unit of the ventilator by a measuring maneuver with detection of the pressure situation by measurement in the lungs by means of an esophageal pressure sensor and by detecting the pressure situation on the basis of pressure set values or pressure measured values of the inspiratory and/or expiratory ventilation pressure. These individually determined ratios of stiffness or elasticity of the lungs to the stiffness or elasticity of the respiratory system comprising the lungs and the thorax can be assigned to individual patients as property data and they can be made available to the ventilator and/or to the measuring device when carrying out the RSVT maneuver. These property data may have been obtained chronologically before the application of the RSVT maneuver. For example, these predefined values can be obtained by means of the already described use of the esophageal pressure sensor in combination with pressure set values or pressure measured values of the inspiratory and/or expiratory ventilation pressure. These property data may be stored in data banks or in so-called patient data management systems and they can thus be available to the ventilator and/or to the measuring device by means of, for example, a data network (LAN, WLAN). In addition, possibilities arise for also determining these individual property data by means of alternative methods, for example, by maneuvers carried out by the ventilator to determine the elasticity or the stiffness of the lungs (lung elastance) relative to the elasticity of the respiratory system comprising the lungs and the thorax (overall elastance), which will be described below as subjects of additional preferred embodiments. This leads to the advantage that even when no additional measurement maneuvers are carried out continuously during the ventilation, this embodiment leads to an application of more precise and standardized pressure stages than when the procedure is carried out without estimation of the ratio.

These individual property data may be obtained according to another preferred embodiment, for example, by means of a determination or estimation of the predefined values on the basis of a determination of a difference of the end-expiratory lung volume of the patient at at least two different exhalation pressure levels. Such a possibility of determination and estimation at at least two different exhalation pressure levels is described, for example, in EP 2923641 A1. Without the necessity of an additional sensor and/or esophageal pressure sensor and without having to interfere with the ventilation pattern by special maneuvers, for example, by occlusions, the ratio of the elasticity or stiffness of the lungs (lung elastance) to the elasticity of the respiratory system comprising the lungs and the thorax (overall elastance) can be estimated in this manner. The ratio of the lung elastance to the overall elastance is an indicator of the effect of the ventilation pressure on and into the lungs themselves, on the one hand, as well as on the heart, on the other hand.

These individual property data may also be determined according to another preferred embodiment, for example, by means of a determination or estimation of the predefined values on the basis of a measurement maneuver with the use of an end-expiratory occlusion during the inhalation by the patient. Such a possibility of determination and estimation by means of an occlusion maneuver is described, for example, in EP 1972274 A1. Without the necessity of an additional sensor and/or esophageal pressure sensor and without the necessity of the variation of the end-exhalation pressure, the ratio of the elasticity or stiffness of the lungs (lung elastance) to the elasticity of the respiratory system comprising the lungs and the thorax (overall elastance) can be estimated by this embodiment. The ratio of the lung elastance to the overall elastance is an indicator of the effect of the ventilation pressure on and into the lungs themselves, on the one hand, as well as on the heart, on the other hand.

Even independently from the manner of determination by means of the above-mentioned occlusion maneuvers, derivations from exhalation pressure levels or from the additional pressure sensor, especially also from the esophageal pressure, these individual property data may, according to another preferred embodiment, also be present as stored data, for example, in the form of data sets individually assigned to patients in a data bank system or patient data management system and be made available to the control unit. In addition, individually performed data inputs or stored data on properties of the lungs and thorax, preferably in conjunction with clinical pictures and/or diagnoses, directly as a classification of the ratios of the elasticity or stiffness of the lungs (lung elastance) to the elasticity of the respiratory system comprising the lungs and the thorax (overall elastance), which ratios are available for the patient in question, may also be stored by the clinical staff for patients in the data bank system or in the patient data management system and they may be intended for being made available to the control unit and/or to the clinical user. As an alternative, such data or data inputs may be used as the basis for classifications concerning the ratios of the elasticity or stiffness of the lungs (lung elastance) to the elasticity of the respiratory system comprising the lungs and the thorax (overall elastance), which ratios are available for that patient, and the control unit is then able on the basis of these ratios to determine the predefined values for checking and raising the pressure levels and for checking the time periods for the performance of the RSVT maneuver. Classifications may be configured here in a simple embodiment in three steps as a classification of the individual lung type, and they may be estimated by the user, for example, as "stiff," "normal" and "soft" lung properties, and they may have been stored by the user in the data bank system or in the patient data management system. Even such a three-step classification would make it possible individually to adjust the exemplary pressure increases for the "normal" classification from 10 cmH$_2$O to 20 cmH$_2$O and then to 30 cmH$_2$O relative to the pressure level given or set for the patient at the start of the maneuver. The following adjustment with pressure stages from 8 cmH$_2$O to 18 cmH$_2$O and then to 28 cmH$_2$O is obtained for the "stiff" classification. The adaptation with pressure stages from 12 cmH$_2$O to 22 cmH$_2$O and then to 32 cmH$_2$O relative to the pressure level given or set at the start of the maneuver is obtained for the "soft" classification.

In other preferred embodiments of the ventilator, the control unit is configured to take into consideration during the control of the inhalation valve and/or of the exhalation valve the measured value that indicates a pressure level inside the patient. To apply the ventilation pressures during the pressure stages of the RSVT maneuver, the control unit is configured, for example, to also take into consideration the measured value of the additional pressure sensor during the control of the ventilation pressure ($P_{AW}$) in addition to the set point of the desired pressure increase during the phase of inhalation of the RSVT maneuver. In one variant, the control unit can use here during the phase of inhalation the measured value of the esophageal pressure sensor as a controlled variable for the pressure regulation of the ventilation pressure ($P_{AW\_insp}$) by means of the inhalation valve and of the exhalation valve.

In another embodiment, the control unit additionally takes into consideration during the phase of inhalation, in addition to the measured value of the esophageal pressure sensor, the measured value, which indicates an airway pressure ($P_{AW}$) of the patient, especially the measured value of the inhalation pressure sensor ($P_{insp}$) as an additional controlled variable. Such an additional consideration offers possible advantages of a further individualization of the pressure stages of the RSVT maneuver directly during the operation during the ventilation of the patient, and changes over the course, such as acutely occurring changes in the lung elastance and/or in the overall elastance and hence also in the ratio of the elasticity or stiffness of the lungs (lung elastance) to the elasticity of the respiratory system comprising the lungs and the thorax (overall elastance), can also be compensated in real time. An adjustment or regulation of the pressure stages of the RSVT maneuver is made possible for the next RSVT maneuver. In addition, it also makes possible an adjustment or pressure regulation during the application of the pressure stages in the course of an RSVT maneuver quasi in real time (online). In such an embodiment, the esophageal pressure sensor as an additional pressure sensor in addition to the inspiratory and/or exhalation pressure sensor then controls the control and/or regulation of the pressure stages of the inspiratory ventilation pressure during the RSVT maneuver. Based on the example of the "normal" classification" from 10 cmH$_2$O to 20 cmH$_2$O and then to 30 cmH$_2$O relative to the pressure level given or set at the start, an individual compensation of the pressure stages can be carried out by the control unit to (10 cmH$_2$O+ΔP1), then to (20 cmH$_2$O+ΔP2) and then to (30 cmH$_2$O+ΔP3). Changes occurring over time as acute or long-term changes in the lung elastance and/or in the overall elastance may be caused, for example, by additional illnesses, side effects of the underlying disease, changes in medication, repositioning of the patient, changes in the ventilation settings and ventilation modes. and progression of the recovery process.

According to another aspect of the present invention, a system having functions of a ventilator and a physiological patient monitor is configured to carry out a maneuver influencing the inhalation pressure P$_{insp}$ with at least two inhalation pressure levels, which maneuver is synchronized with a measuring device. The system has a ventilator for ventilating a patient and a physiological patient monitor device as a measuring device for detecting physiological values of the same patient. The measuring device is arranged in or at the system or such a measuring device is associated with the system. The measuring device is configured for measured value acquisition by means of a control unit and of additional components (amplifier, analog-to-digital converter) for detecting by measurement a data set of invasive and/or non-invasive blood pressure measured values of a patient. The ventilator has a data interface. The measuring device likewise has a data interface. The data interfaces of the measuring device and of the ventilator are configured and intended for providing and implementing a wired and/or wireless communication with one another. The data interfaces of the measuring device and of the ventilator may, moreover, be configured and intended for receiving external data or additional data, for example, also predefined values for carrying out the RSVT maneuver. The communication provides a coordinated operation between the ventilator and the measuring device with a synchronization in time of the control of the inspiratory pressure level P$_{insp}$ with the measurement-based detection of the data set of invasive and/or non-invasive blood pressure measured values P$_{BP}$. Such a system offers, for example, many advantages in order to make it possible to configure the communication and the data exchange between the ventilator and the measuring device with the shortest possible time lag. Such a system also offers the advantage that the analysis can take place in real time and the values of ventilation pressures effective for obtaining the RSVT maneuver and the ventilation pressures to be applied, which are necessary for this, can be readily assigned chronologically to the result.

In a preferred embodiment of the system, the communication is carried out unidirectionally or bidirectionally between the ventilator and the measuring device, and the ventilator controls during the coordinated operation a maneuver with detection of the data set of invasive and/or non-invasive blood pressure measured values P$_{BP}$ determined by the measuring device. This control of the measuring device by the ventilator offers, for example, the advantages that the ventilator sets the time at which the RSVT maneuver is carried out and it can thus also be integrated into and coordinated with the course of the ventilation and thus, for example, with the clinical procedure with usually necessary, repeatedly necessary suctioning of secretion from the lungs and from the bronchial tract. The ventilator plays a leading role in the communication between the ventilator and the measuring device. The ventilator plays quasi the role of a "master" in this hierarchic communication concept, while the role of a "slave" can quasi be assigned to the measuring device.

In a preferred embodiment of the system, the communication is carried out unidirectionally or bidirectionally between the ventilator and the measuring device, and the measuring device controls during the coordinated operation a maneuver with control of the pressure level of the inhalation pressure P$_{insp}$ by means of the inhalation valve and with control of the pressure level of the exhalation valve by the ventilator. The measuring device plays the leading role in the communication between the measuring device and the ventilator. The measuring device plays quasi the role of a "master" in this hierarchic communication concept, while the role of a "slave" can be assigned to the ventilator. This control of the ventilator by the measuring device offers, for example, the advantages that based on the course of the physiological monitoring, for example, directly and without undue delay, at the time at which it is necessary to make a therapeutic decision on whether liquid shall be additionally administered to the patient and in what quantity, the RSVT maneuver can be started directly at the measuring device in order to determine a current state of the fluid responsiveness.

In a preferred embodiment of the system, the communication is carried out unidirectionally or bidirectionally between the ventilator and an external control unit and/or unidirectionally or bidirectionally between the measuring device and an external control unit. During the coordinated operation, the external control unit controls a maneuver with control of the pressure level by the ventilator, with control of the inhalation pressure P$_{insp}$ by means of the inhalation valve and with control of the exhalation pressure level by control of the exhalation valve by the ventilator. The external control unit plays a leading role here in the communication between the measuring device and the ventilator. The external control unit likewise plays the role of a "master" in this hierarchic communication concept, while the role of a "slave" can be quasi assigned to the ventilator and to the measuring device. This control of the ventilator by the external control unit makes possible, for example, the advantage of a remote control of the ventilator, i.e., starting of the maneuver remotely from the location at which the patient is being treated, for example, from a central monitoring room, such as a nurse station or a physician's office.

In a preferred embodiment, the system is configured such that the communication is carried out unidirectionally or bidirectionally between the ventilator and an external control unit and/or unidirectionally or bidirectionally between the measuring device and an external control unit. During the coordinated operation, the external control unit controls a maneuver with detection of the data set of invasive and/or non-invasive blood pressure measured values by the measuring device. The external control unit plays a leading role here in the communication between the measuring device and the ventilator. The external control unit plays quasi the role of a "master" in this hierarchic communication concept, while the role of a "slave" can be assigned to the ventilator and to the measuring device. This control of the measuring device by the external control unit makes possible, for example, the advantage of a remote control of the measuring device, i.e., a start of the maneuver remotely from the location at which the patient is being treated, for example, from a central monitoring room, such as a nurse station or a physician's office.

In another preferred embodiment, the system is configured such that the communication is carried out unidirectionally or bidirectionally between the ventilator and an external control unit and/or unidirectionally or bidirectionally between the measuring device and an external control unit. During the coordinated operation, the external control unit coordinates the detection of the data set of invasive and/or non-invasive blood pressure measured values and at the same time a control of the pressure level of the inhalation pressure $P_{insp}$. The external control unit plays a leading role here in the communication between the measuring device and the ventilator. The external control unit plays quasi the "master" role in this hierarchic communication concept, while the role of a "slave" can be assigned to the ventilator and also to the measuring device. This control of the ventilator and of the measuring device by the external control unit makes possible, for example, the advantage of a remote control of the ventilator and of the measuring device, i.e., a start of the maneuver remotely from the location at which the patient is being treated, for example, a remote control of the RSVT maneuver by means of a computer-assisted input device, for example, a personal computer or laptop from a central monitoring room or in a location-independent manner during the mobile work of the clinical staff by means of a tablet PC or smartphone.

In a preferred embodiment, the system has an analysis unit, which is arranged in or at the system or is associated with the system. The analysis unit is configured to determine and to provide a slope value $Slope_{RSVT}$. The detected blood pressure measured values are synchronized in time by the RSVT maneuver carried out previously with the pressure levels of the inhalation pressure $P_{insp}$. The determination of the slope value $P_{RSVT}$ is carried out with the formation of a quotient from a difference of the blood pressure measured values detected during the maneuver by the measuring device and a difference of the pressure level of the inhalation pressure $P_{insp}$, which was set by the ventilator during the maneuver. This provision of the slope value $Slope_{RSVT}$ offers a relief to the user, for example, a physician in the intensive care unit, in the diagnosis and in the daily routine and monitoring. This preferred embodiment of the system offers, for example, the following advantages—in addition to the measured value acquisition and the carrying out of the maneuver by the control unit—that the analysis unit offers, in addition, a possibility of data analysis with calculation of the slope value $Slope_{RSVT}$. The analysis unit can, moreover, also carry out optionally a classification of the patient to different patient types on the basis of the slope value $Slope_{RSVT}$ and make it available to the user. A classification as "fluid responder" and "non-responder" shall be mentioned as an example. The analysis unit and the control unit are often configured jointly as a computer.

In a preferred embodiment, the analysis unit in the system is configured to use arterial systolic blood pressure measured values from the data set of invasive and/or non-invasive blood pressure measured values during the determination of the slope value $Slope_{RSVT}$ with measured values of the pressure level of the inhalation pressure $P_{insp}$, which are synchronized therewith in time.

In a preferred embodiment, an output unit is arranged in or at the system or an output unit is associated with the system, the output unit being configured and intended to receive and to make available the slope value determined and provided by the analysis unit. Forwarding to the user, for example, by means of an alphanumeric or graphic output as well as an automated provision to the electronic patient file, e.g., in a patient data management system, is made possible in this manner. This provision in the patient data management system then makes it possible for different users from different locations to be able to access the results of the RSVT maneuvers performed during the clinical operation.

The present invention will now be explained in more detail by means of the following figures and the corresponding descriptions of the figures without limitation of the general inventive idea. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
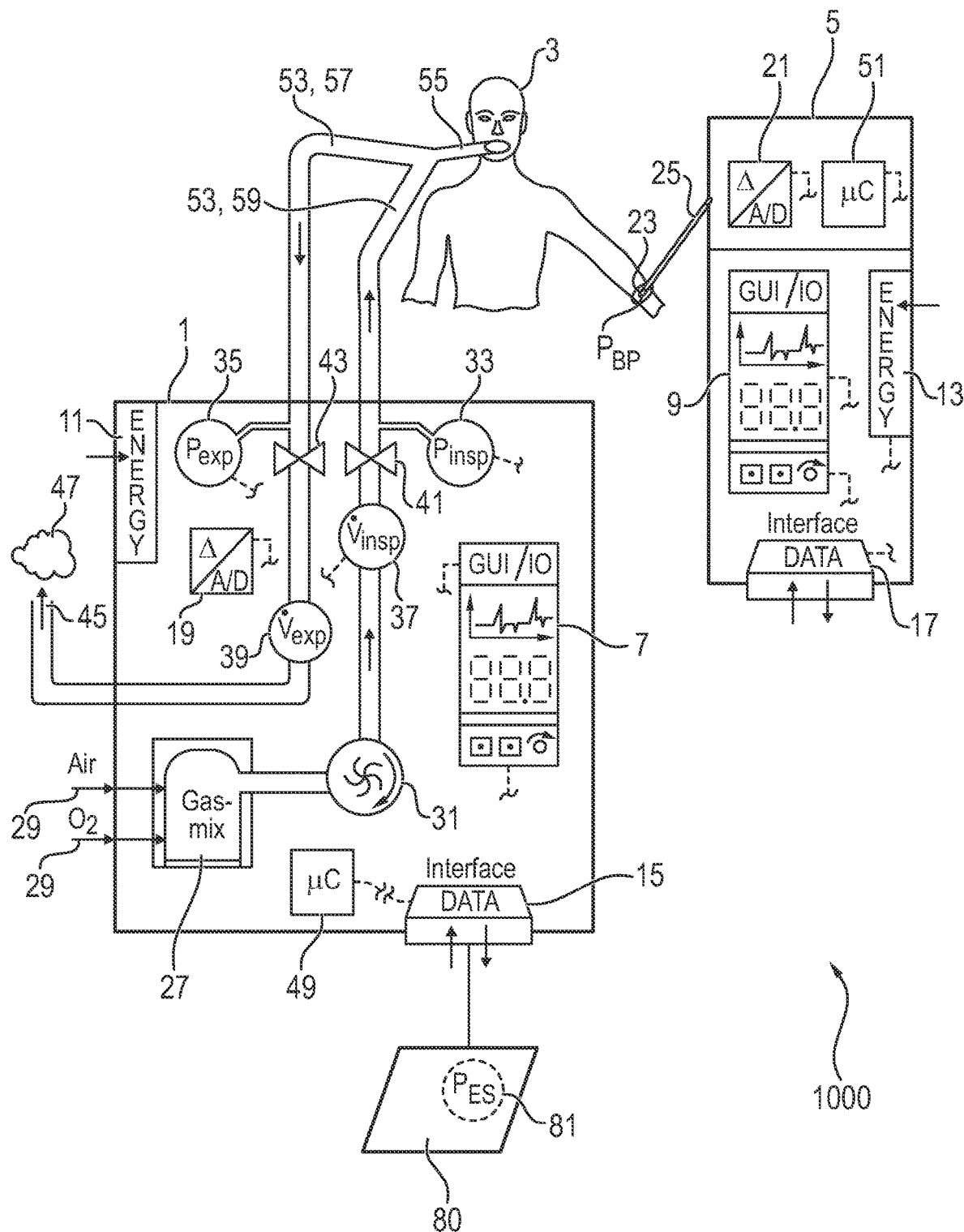
FIG. 1 is a first schematic view of a system comprising a ventilator and a measuring device.

Referring to the drawings, FIG. 1 shows a first schematic view of a system 1000 comprising a ventilator 1 and a measuring device 5 during application at a patient 3. A system 1000, which shows the ventilator 1 and the measuring device 5 as well as the patient 3 in interaction with the components involved, is shown schematically in FIG. 1. The ventilator 1 has an input and output unit 7, an energy interface 11, a data interface 15, a signal processing unit 19, a gas mixer 27, a gas feed 29 for feeding air and oxygen, a ventilation drive 31, an inhalation pressure sensor 33, an exhalation pressure sensor 35, an inhalation flow sensor 37, an exhalation flow sensor 39, an inhalation valve 41, an exhalation valve 43 and a gas outlet 45 for exhaled gases to an environment 47. In addition, the ventilator 1 has a control unit 49. The control unit 49 is configured and intended for control, regulation, checking and data exchange with the components input and output unit 7, data interface 15, signal processing unit 19, ventilation drive 31, pressure sensors 33, 35, flow sensors 37, 39, valves 41, 43. The control unit 51 controls the ventilation in order to send gases via a connection system (ventilation tube system) 53 to the patient 3 and to remove them from the patient. The connection system (ventilation tube system) 53 has an inhalation tube 57 for sending the breathing gases from the ventilator 1 to the patient 3, as well as an exhalation tube 59 for returning the breathing gases from the patient 3 to the ventilator 1. The inhalation tube 57 and the exhalation tube 59 are connected close to the patient via a connection element 55 (Y-piece). The gas exchange with the patient 3 takes place from this connection element 55 via an endotracheal tube, not shown in this FIG. 1, or via a breathing mask or a tracheostoma (tracheal access), likewise not shown. The ventilator 1 provides with the components described a basic functionality for ventilating a patient 3. This includes the possibility of making possible settings and displays via an input and output unit 7. Thus, a user can make, for example, settings for the ventilation, such as the ventilation rate (respiratory rate, RR), tidal volume, inhalation and exhalation pauses, inhalation to exhalation ratio (I:E ratio), inhalation pressure, exhalation pressure. The control unit 49 of the ventilator 1 then controls, i.e., controls and/or regulates the components, such as the gas mixer 27, the ventilation drive 31, the inhalation valve 41, the exhalation valve 43, on the basis of measured data obtained from the sensors 33, 35, 37, 39 by means of the signal processing unit 19. The measuring device 5 provides, together with the signal processing unit 21, in combination with the blood pressure measuring line 25, a possibility for measuring the blood pressure of the patient 3. In an embodiment of the measuring device 5 as a physiological monitor, additional measured variables, for example, temperatures, EKG, $SPO_2$, can also be detected at the patient 3 by the measuring device 5 in addition to the invasive (IBP) and non-invasive (NIBP) blood pressure. Both the measuring device 5 and the ventilator 1 are supplied with electrical energy, i.e., supply voltage, for example, from the 230-V a.c. grid or from a portable battery or rechargeable battery unit through energy interfaces 13, 11. Signal and data connections, in the ventilator 1 and in the measuring device 5 between the control units 49, 51 and the components, for example, signal processing units 19, 21, pressure sensors 33, 35, flow sensors 37, 39, valves 41, 43, are suggested in this FIG. 1 by means of indicated broken lines, for example, at the input and output units 7, 9, and are designated by reference numbers 70, 90 at these lines, but the connections between the components are not shown consistently in order to preserve the clarity of the view.

This also applies to the view of the supply lines from the energy interfaces 11, 13 to the components 7, 9, 15, 17, 19, 21, 27, 31, 33, 35, 37, 39, 41, 43, 49, 51 of the ventilator 1 and of the measuring device 5, which are likewise suggested only at the energy interfaces 11, 13 and are not always led to the components, in order to preserve the clarity of the graphic view. It is possible via the data interfaces 15, 17 to combine the ventilator 1 and the measuring device 5 for a cooperation or for an interaction. Such a cooperation may be configured, for example, such that the ventilator 1 controls the measuring device 5 via the data interfaces 15, 17 for detecting blood pressure measured values. The measuring device 5 or the control unit 51 of the measuring device 5 then starts a detection of blood pressure measured values at a measuring point 23 for the blood pressure measurement at the patient 3 followed by processing in the signal processing unit 21 of the measuring device 5. The measurement of the blood pressure ($P_{BP}$) 83 at the measuring point 23 at the patient 3 may be carried out, for example, via a blood pressure measuring line 25 in the form of a non-invasive pressure measurement. In case of a non-invasive blood pressure measurement (NIBP), the measurement is carried out by means of a sphygmomanometer cuff on the arm or wrist of the patient 3, and the sphygmomanometer cuff is pumped up with air pressure at the measuring point 23 by an air pump, which is present in the measuring device 5 and is not shown in this FIG. 1. Both the diastolic blood pressure and the systolic blood pressure are measured by means of an analysis of the air pressures generated and measured in the sphygmomanometer cuff, in the blood pressure measuring line 25 as well as in the air pump and are made available as a measured value ($P_{BP}$) 83 by the control unit 51 of the measuring device 5 as a value of the non-invasive blood pressure measurement (NIBP). The measurement of the blood pressure ($P_{BP}$) 83 at the measuring point 23 at the patient 3 may be carried out as an alternative—and preferably for an application with an RSVT maneuver—in the form of an invasive pressure measurement. A quantity of blood is sent now from the measuring point 23 invasively from the patient 3 via a blood pressure measuring line 25 to the measuring device 5 and the invasive blood pressure measured value (IBP) is then determined and provided by means of an analysis—not shown as elements or components in FIG. 1—directly in the blood in conjunction with the signal processing unit 21 of the measuring device 5 and with the control unit 51 of the measuring device 5. A cooperation between the measuring device 5 and the ventilator 1 may also be configured, for example, such that the measuring device 5 controls the ventilator 1 via the data interfaces 15, 17 for starting a maneuver. It is possible in this manner that the measuring device 5 will then bring about the RSVT maneuver with an increase in the pressure stages of the inhalation pressure at the ventilator 1 at suitable times of the blood pressure measurement. Due to this cooperation— be it controlled predominantly by the measuring device 5 or be it controlled predominantly by the ventilator 1—synchronization of the blood pressure measurement at the measuring device 5 is possible with the control of the ventilation, i.e., the control of the ventilator 1 and with the components relevant for the ventilation, such as the ventilation drive 31, the pressure sensors 33, 35, the flow sensors 37, 39, as well as the inhalation valve 41 and the exhalation valve 43. One of the control units 49, 51 now assumes the coordination and the cooperation of the RSVT maneuver. Further and alternative possibilities of cooperation and coordination, for example, with the involvement of an external control unit 61 (FIG. 2), are described in FIG. 2. Property data 80, which can indicate properties of the lungs, for example, individual stiffnesses or elasticities of the lungs and/or thorax of the patient 3 or a ratio of an elasticity or stiffness of the lungs (lung elastance) to an elasticity of the respiratory system comprising the lungs and the thorax (overall elastance) of the patient 3, are provided in the system 1000. Such property data can be determined, for example, by means of an esophageal pressure sensor 81, which is suggested as an optional component with broken lines in this FIG. 1, and be processed to make them available.

Figure 2:
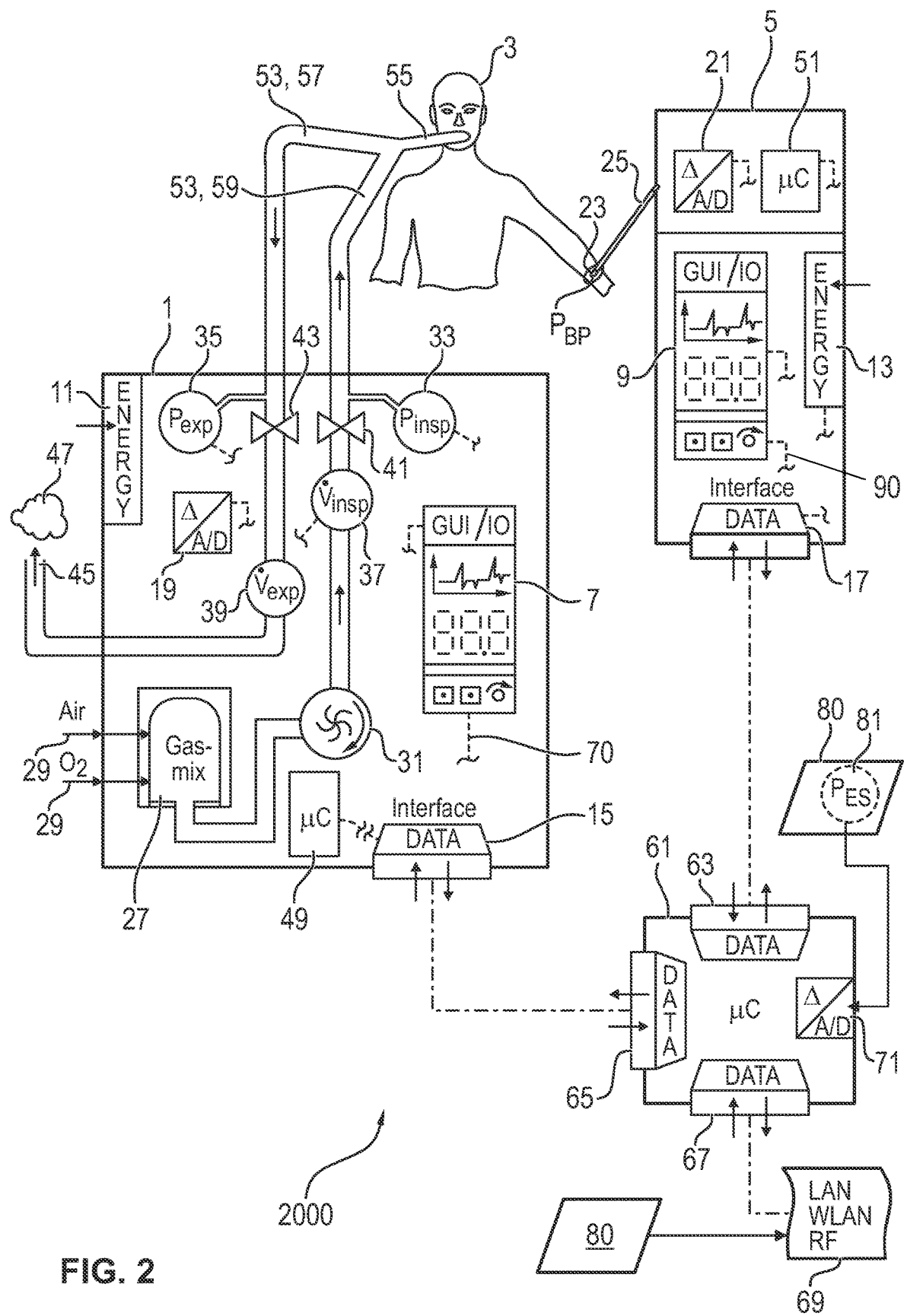
FIG. 2 is a second schematic view according to FIG. 1.

FIG. 2 shows in a second schematic view a system 2000 comprising a ventilator 1 and a measuring device 5 as applied at a patient 3 in cooperation with an external control unit 61, which is obtained as an expansion of the system 1000 according to FIG. 1. Identical components in FIG. 1 and in FIG. 2 are designated by the same reference numbers in FIGS. 1 and 2. An external control unit 61 is present in addition to the components shown in FIG. 1. The external control unit 61 is configured and intended to control in this system 2000 the ventilator 1 as well as the measuring device 5 for a control of the RSVT maneuver. The external control unit 61 controls both the increase in the pressure stages during the performance of the ventilations by the ventilator 1 and the measurement-based detection of the non-invasive or also invasive blood pressure by the measuring device 5. Property data 80, which can indicate properties of the lungs, for example, individual stiffnesses or elasticities of the lungs and/or of the thorax of the patient 3 or a ratio of an elasticity or stiffness of the lungs (lung elastance) to an elasticity of the respiratory system comprising the lungs and the thorax (overall elastance) of the patient 3, are provided in the system 2000. Such property data can be determined, for example, by means of an esophageal pressure sensor 81 in conjunction with a signal processing unit 71 and with the external control unit 61. In addition to a communication between the ventilator 1 and the measuring device 5, which is brought about by means of the data interfaces 15, 17, the external control unit 61 as well as a signal processing unit 71 arranged at the external control unit 61 or associated with the external control unit 61 can also be included in the communication via an additional data interface 63, 65. A connection to a data network 69, which also makes possible, for example, a data exchange with a patient data management system, and which may be configured and intended for the storage and for the provision of the property data 80 and/or of data pertaining to the patient 3 (age, body weight, sex, height, clinical picture, diagnoses, therapy, medication), is made possible via an additional data interface 67.

Figure 3:
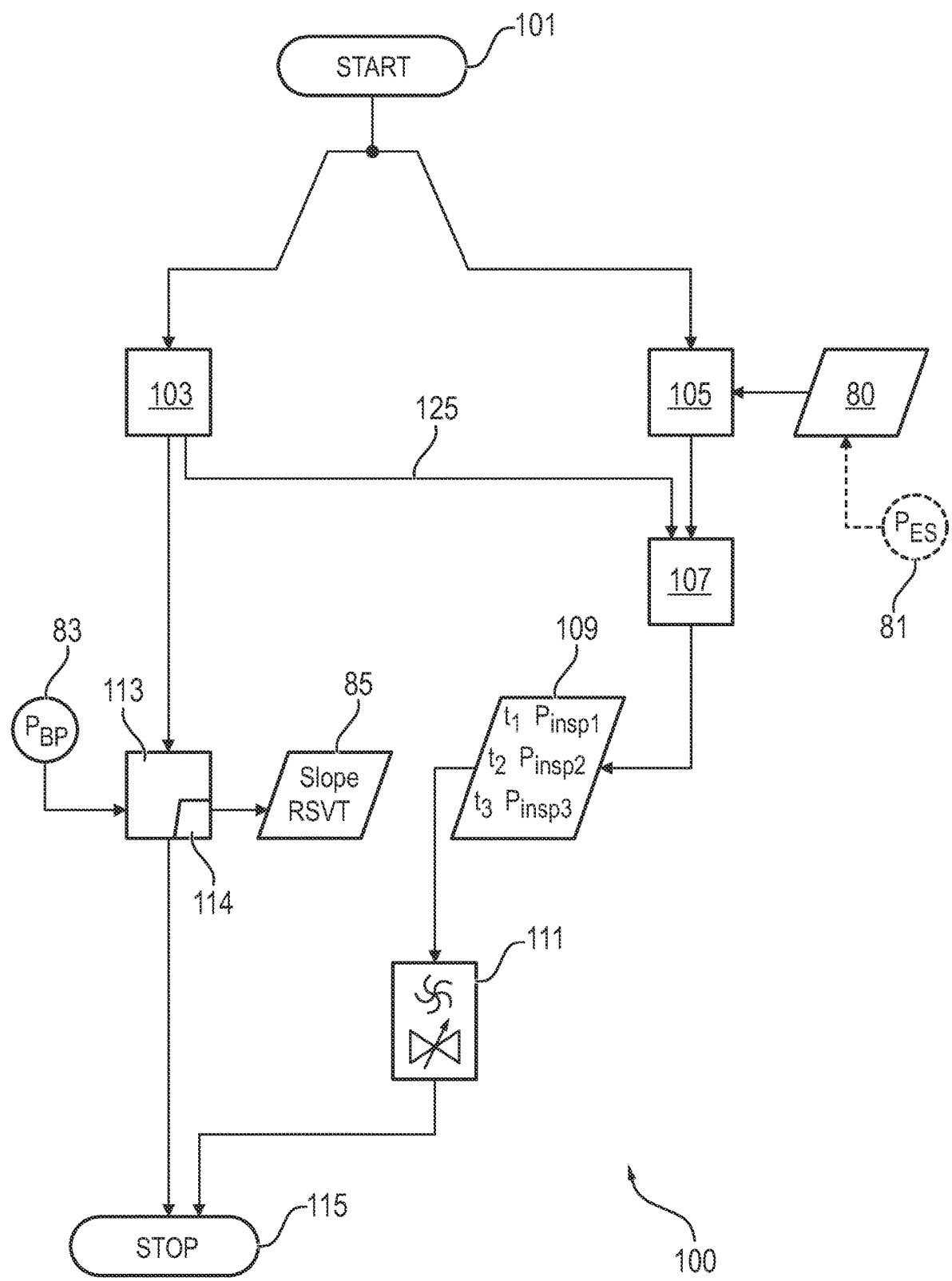
FIG. 3 is a flow chart of an RSVT maneuver.

FIG. 3 shows a first flow chart 100 for the performance of an RSVT maneuver. Identical components in FIGS. 1, 2 and in FIG. 3 are designated by the same reference numbers in FIGS. 1, 2 and 3. Following a START 101, a preparation 103 for a maneuver (first step) is carried out in this FIG. 3 on the ventilator 1 (FIG. 1) and a preparation 105 is carried out for a maneuver (second step) at the measuring device 5 (FIG. 1). In process 100, the measuring device 5 (FIG. 1) carries out a control 125 of the second step 105 at the ventilator 1 (FIG. 1). In step 105, a data set 80 containing property data is read during the preparation for the maneuver at the ventilator 1 (FIG. 1), and inhalation pressure stages are then determined from this data set by the control unit 49 (FIG. 1) of the ventilator 1 (FIG. 1) in the third step 107, and these inhalation pressure stages are then provided in the fourth step 109 as a data set containing inhalation pressure stages and corresponding time periods. Dispensing of the inspiratory ventilation pressure $P_{insp}$ is carried out in the fifth step 111 by the ventilator 1 (FIG. 1) at the patient 3 (FIG. 1). Detection of the blood pressure measured values $P_{BP}$ 83 by the measuring device 5 (FIG. 1) is carried out in a sixth step 113. A result $Slope_{RSVT}$ 85 of the RSVT maneuver is determined and made available from these blood pressure measured values $P_{BP}$ 83 in a seventh step 114. After carrying out the dispensing 111 of all pressure stages of the inspiratory ventilation pressure $P_{insp}$ by the ventilator 1 (FIG. 1), after detection 113 of the corresponding blood pressure measured values $P_{BP}$ 83 by the measuring device 5 (FIG. 1) and after determination of the test result 85, the end 115 of the process 100 is reached and the ventilation is returned to the manner of ventilation that was carried out prior to the start 101 of the RSVT maneuver at the patient 3 (FIG. 1). The property data 80, which can indicate properties of the lungs, for example, individual stiffnesses or elasticities of the lungs and/or of the thorax of the patient 3 or a ratio of an elasticity or stiffness of the lungs (lung elastance) to an elasticity of the respiratory system comprising the lungs and the thorax (overall elastance) of the patient 3, are included in the process 100 for the determination 107 and for the provision 109 of the inhalation pressure levels and of the corresponding time periods. Such property data 80 can be determined, for example, by means of an esophageal pressure sensor 81, which is suggested in this FIG. 3 with broken lines as a possible and optional variant component.

Figure 4:
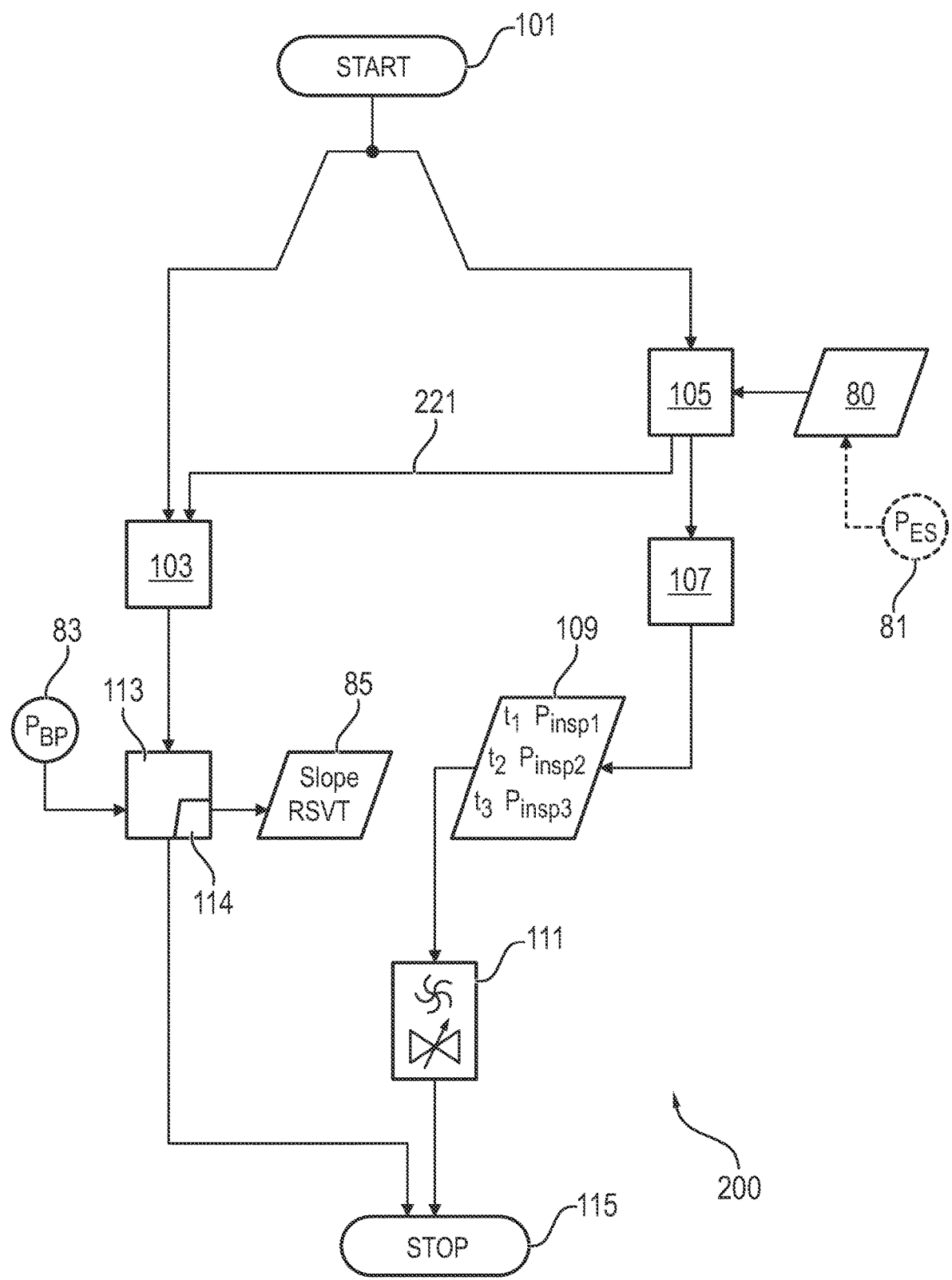
FIG. 4 is an alternative flow chart variant according to FIG. 3.

FIG. 4 shows a second flow chart 200 of an RSVT maneuver. Identical components in FIGS. 1, 2, 3 and in FIG. 4 are designated by the same reference numbers in FIGS. 1, 2, 3 and 4. A preparation 103 for a maneuver is carried out at the ventilator 1 (FIG. 1) in this FIG. 4 after a START 101 and a preparation 105 for a maneuver is carried out at the measuring device 5 (FIG. 1). In the process 200, a control 221 of the preparation 105 for the maneuver is carried out at the measuring device 5 (FIG. 1) with the preparation 103 for the maneuver at the ventilator 1 (FIG. 1). A data set 80 containing property data is read with the preparation for the maneuver at the ventilator 1 (FIG. 1), and the control unit 49 (FIG. 1) of the ventilator 1 (FIG. 1) determines 107 inhalation pressure levels from this data set, and these inhalation pressure levels are then provided as a data set 109 with inhalation pressure stages and with corresponding time periods. A dispensing 111 of the inspiratory ventilation pressure $P_{insp}$ is then carried out by the ventilator 1 (FIG. 1) at the patient 3 (FIG. 1). Detection 113 of blood pressure measured values $P_{BP}$ 83 is then carried out by the measuring device 5 (FIG. 1). A determination 114 and provision of a result $Slope_{RSVT}$ 85 of the RSVT maneuver are then carried out from these blood pressure measured values $P_{BP}$ 83. After carrying out the dispensing 111 of all pressure stages of the inspiratory ventilation pressure $P_{insp}$ by the ventilator 1 (FIG. 1), after detection 113 of the corresponding blood pressure measured values $P_{BP}$ 83 by the measuring device 5 (FIG. 1) and after determination of the test result 85, the end 115 of the process 200 is reached and the process is returned to the manner of ventilation that was carried out prior to the start 101 of the RSVT maneuver at the patient 3 (FIG. 1). The property data 80, which can indicate properties of the lungs, for example, individual stiffnesses or elasticities of the lungs and/or thorax of the patient 3 or a ratio of an elasticity or stiffness of the lungs (lung elastance) to an elasticity of the respiratory system comprising the lungs and the thorax (overall elastance) of the patient 3, are included in the process 200 for the determination 107 and for the provision 109 of the inspiratory pressure stages and of corresponding time periods. Such property data 80 can be determined, for example, by means of an esophageal pressure sensor 81 suggested in this FIG. 4 with broken lines as a possible and optional variant component.

Figure 5:
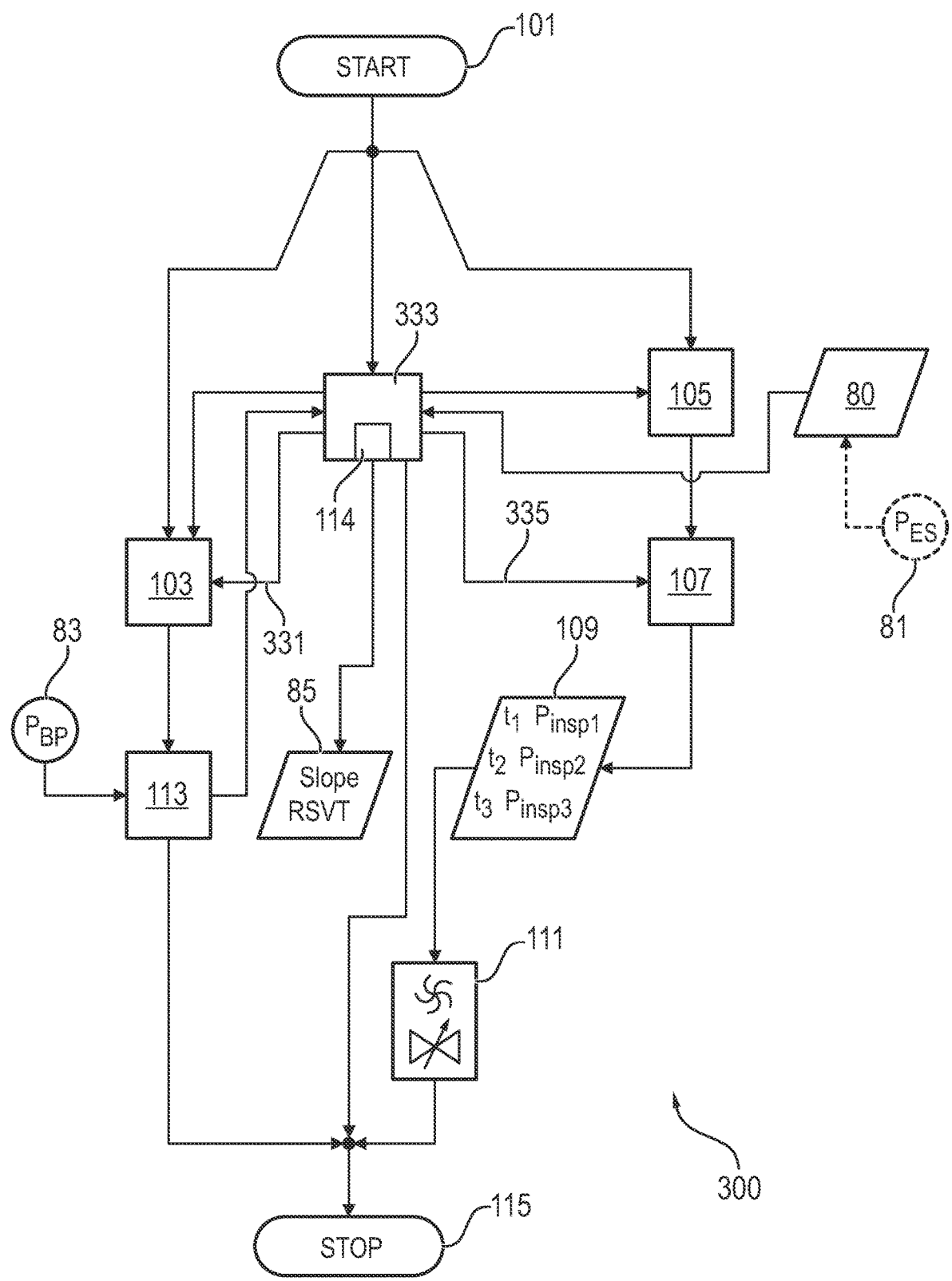
FIG. 5 is another alternative flow chart variant according to FIG. 3.

FIG. 5 shows a third flow chart 300 of an RSVT maneuver with an external control of the maneuver. Identical components in FIGS. 1, 2, 3, 4 and in FIG. 5 are designated by the same reference numbers in FIGS. 1, 2, 3, 4 and 5. An external maneuver control 333 of the process 300 takes place in process 300 after a START 101 in this FIG. 5. Maneuver preparation 103 at the ventilator 1 (FIG. 2) and maneuver preparation 105 at the measuring device 5 (FIG. 2) are carried out by means of control commands 331, 335 by the external maneuver control 333. Such an external maneuver control 333 may be carried out, for example, by an external control unit 61 (FIG. 2). The manner of interaction of an external control unit 61 (FIG. 2) with the control units 49, 51 (FIG. 2) of the ventilator 1 (FIG. 2) and with the measuring device 5 (FIG. 2), and also with a data network is shown in FIG. 2. A data set 80 containing property data, from which data set a determination 107 of inspiratory pressure stages is carried out, is read with the external maneuver control 333 of the maneuver preparations 103, 105, and these pressure stages are then provided as a data set 109 with inspiratory pressure stages and corresponding time periods. Both an activation of the dispensing 111 of the inspiratory ventilation pressure $P_{insp}$ and a detection 113 of blood pressure measured values $P_{BP}$ 83 are carried out subsequently by means of the external maneuver control 333. A determination 114 and provision of a result $Slope_{RSVT}$ 85 of the RSVT maneuver are carried out from these blood pressure measured values $P_{BP}$ 83. After carrying out the dispensing 111 of all pressure stages of the inspiratory ventilation pressure $P_{insp}$, detection 113 of the corresponding blood pressure measured values $P_{BP}$ 83 and determination of the test result 85, the end 115 of the process 300 with external control of the RSVT maneuver is reached. Inclusion of the property data 80, which can indicate properties of the lungs, for example, individual stiffnesses or elasticities of the lungs and/or thorax of the patient 3 or a ratio of an elasticity or stiffness of the lungs (lung elastance) to an elasticity of the respiratory system comprising the lungs and the thorax (overall elastance) of the patient 3, is carried out in process 300 for the determination 107 and the provision 109 of the inspiratory pressure stages and corresponding time periods. Such property data 80 can be determined, for example, by means of an esophageal pressure sensor 81 suggested in this FIG. 5 with broken lines as a possible and optional variant component.

Figure 6:
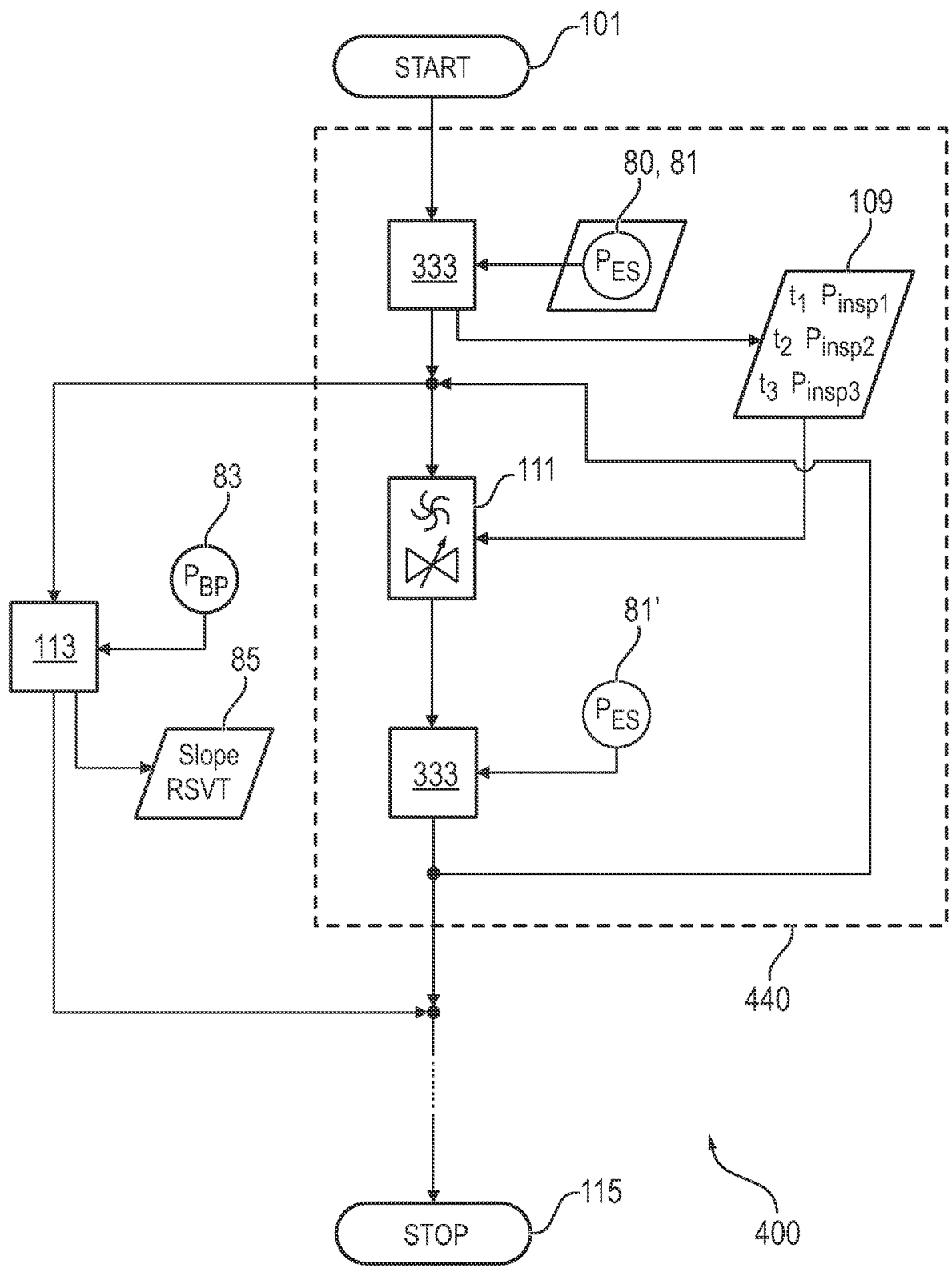
FIG. 6 is a variation of an RSVT maneuver according to FIG. 5.

FIG. 6 shows a fourth flow chart 400 of an RSVT maneuver, which is to be defined as a variation of the possibilities of carrying out the RSVT maneuver, which are shown in FIGS. 3, 4, and 5.

Identical components in FIGS. 1, 2, 3, 4, 5 and in FIG. 6 are designated by the same reference numbers in FIGS. 1, 2, 3, 4, 5 and 6. Similarly to what is shown and described in connection with FIG. 5, an external control 333 of the RSVT maneuver is carried out in process 400. Such an external control 333 may be carried out, for example, by an external control unit 61 (FIG. 2). The manner of interaction of an external control unit 61 (FIG. 2) with the control units 49, 51 (FIG. 2) of the ventilator 1 (FIG. 2) and measuring device 5 (FIG. 2), and also with a data network, is shown in FIG. 2. Current measured values 81' of an esophageal pressure sensor 81 are detected or read with the external control 333 of the maneuver preparation, optionally in connection with a data set 80 containing property data of the patient 3 (FIG. 2), and a determination 107 of inspiratory pressure stages is carried out, and these pressure stages are then provided as a data set 109 with inspiratory pressure stages and corresponding time periods. Then, both an activation and control of the dispensing 111 of the inspiratory ventilation pressure $P_{insp}$ and a detection 113 of blood pressure measured values $P_{BP}$83 are carried out by means of the external control 333. A determination 114 and provision of a result 85 of the RSVT maneuver are carried out from these blood pressure measured values $P_{BP}$83. The manner of activation and control 440 of the dispensing 111 of the inspiratory ventilation pressure $P_{insp}$ is carried out in process 400 according to this FIG. 6 as a control or regulation based on the measured values 81' of the esophageal pressure sensor 81. The control 440 of the dispensing 111 of the inspiratory ventilation pressure $P_{insp}$ may be carried out either in the form of a control (open loop control) or as a regulation in a closed loop (closed loop control) based on current measured values 81' of the esophageal pressure sensor in reference to a target value of the inspiratory ventilation pressure $P_{insp}$, which target value is determined from the property data 80. After carrying out the control or regulation of the dispensing 111 of all pressure stages of the inspiratory ventilation pressure $P_{insp}$ with continuous detection of current measured values 81' of the esophageal pressure sensor 81, detection 113 of the corresponding blood pressure measured values $P_{BP}$ 83 and determination of the test result 85 the end 115 of the process 400 with external control of the RSVT maneuver is reached.

While specific embodiments of the invention have been shown and described in detail to illustrate the application of the principles of the invention, it will be understood that the invention may be embodied otherwise without departing from such principles.

LIST OF REFERENCE NUMBERS

1 Ventilator (respirator)
3 Patient
5 Measuring device (physiological patient monitor, PPM)
7 Input and output unit of the ventilator
9 Input and output unit of the measuring device
11 Energy interface of the ventilator
13 Energy interface of the measuring device
15 Data interface (interface) of the ventilator
17 Data interface (interface) of the measuring device
19 Signal processing unit of the ventilator
21 Signal processing unit of the measuring device
23 Measuring point for blood pressure measurement (BP) at the patient
25 Blood pressure measuring line
27 Gas mixer
29 Gas feed (air and oxygen)
31 Ventilation drive (blower)
33 Inspiratory pressure sensor ($P_{insp}$)
35 Expiratory pressure sensor (Pexp)
37 Inspiratory flow sensor
39 Expiratory flow sensor
41 Inhalation valve
43 Exhalation valve
45 Gas outlet for exhaled gases
47 Environment
49 Control unit of the ventilator
51 Control unit of the measuring device
53 Connection system (ventilation tube system)
55 Connection element (Y-piece)
57 Inhalation tube
59 Exhalation tube
61 External control unit
63, 65, 67 Data interfaces of the external control unit
69 Data network
70 Data and signal lines of the ventilator
71 Signal processing unit in/at the external control unit
80 Predefined values, data set containing property data
81 Esophageal pressure sensor, pressure measured values (PES)
81' Current measured values (PES) of the esophageal pressure sensor
83 Blood pressure sensor, pressure measured values ($P_{BP}$)
85 Test result ($Slope_{RSVT}$)
90 Data and signal lines of the measuring device
100 First flow chart
101 Start
103 Preparation for maneuver, step 1 (control unit)
105 Preparation for maneuver, step 2 (control unit)
107 Determination of inspiratory pressure stages, step 3 (control unit)
109 Data set with inspiratory pressure stages and time periods, step 4
111 Dispensing of the ventilation pressure, step 5 (ventilation drive)
113 Detection of blood pressure measured values, step 6 (signal processing unit and/or control unit)
114 Determination of the test result, step 7 (analysis unit)
115 Stop, end
125 Control command of the measuring device to the ventilator
200 Second flow chart
221 Control command of the ventilator to the measuring device
300 Third flow chart
331 Control command from the external control unit to the measuring device
333 External maneuver control
335 Control command from the external control unit to the ventilator
400 Fourth flow chart 440 Control/regulation (open loop control/closed loop control)
1000 System comprising ventilator and measuring device
2000 System comprising external control unit, ventilator and measuring device

What is claimed is:

1. A ventilator for a mechanical ventilation of a patient, the ventilator comprising:
an exhalation valve;
an inhalation valve;
an inspiratory pressure sensor;
an expiratory pressure sensor;
a control unit;
a data interface configured to provide predefined values to the control unit; and
a connection system with an inhalation line for feeding breathing gases to the patient and with an exhalation line for removing breathing gases from the patient, wherein:
the inspiratory pressure sensor is arranged in or at the inhalation line of the connection system;
the inspiratory pressure sensor is configured to detect an inhalation pressure and to provide the inhalation pressure measured value for the control unit;
the expiratory pressure sensor is configured to provide the expiratory pressure measured value for the control unit;
the control unit is configured to control the inhalation valve taking into account the inhalation pressure measured value in order to provide an inspiratory pressure level via the inhalation line of the connection system for the patient;
the control unit is configured to control the exhalation valve taking the expiratory pressure measured values into consideration in order to provide an expiratory pressure level for the patient via the exhalation line of the connection system;
the control unit is configured to control the inhalation valve and the exhalation valve such as to raise the inspiratory pressure level from a first pressure level to a predefined second pressure level during an inspiration phase and to maintain the inspiratory pressure level for a first predefined time period during the inspiration phase;
the control unit is configured to control the inhalation valve and the exhalation valve such as to raise the second pressure level to a predefined third pressure level during the inspiration phase and to maintain the third pressure level for a second predefined time period during the inspiration phase; and
the control unit is configured to take predefined values into consideration during the control of the pressure levels and during the control of the time periods.

2. A ventilator in accordance with claim 1, wherein the control unit is configured to control the inhalation valve and the exhalation valve so as to raise the third pressure level to a predefined fourth pressure level during the inspiration phase and to maintain the fourth pressure level for a third predefined time period during the inspiration phase.

3. A ventilator in accordance with claim 1, wherein the predefined values comprise predefined values for raising the inspiratory pressure level from the first pressure level to the second pressure level and for raising the inspiratory pressure level to the third pressure level.

4. A ventilator in accordance with claim 2, wherein the predefined values comprise predefined values for raising the inspiratory pressure level from the third pressure level to the fourth pressure level.

5. A ventilator in accordance with claim 3, wherein the predefined values comprise the predefined time periods for maintaining the second and third pressure levels.

6. A ventilator in accordance with claim 4, wherein the predefined values comprise the predefined time periods for maintaining the fourth pressure level.

7. A ventilator in accordance with claim 1, further comprising an additional pressure sensor, wherein:
the additional pressure sensor is configured to detect current measured values, which indicate a pressure situation inside the patient and to indirectly and/or directly provide the measured values, which indicate the pressure situation inside the patient, to the control unit; and
the control unit is configured to determine the predefined values based on measured values of the additional pressure sensor or based on measured values of the inspiratory pressure sensor or based on measured values of the expiratory pressure sensor or based on any combination of the measured values of the additional pressure sensor, the measured values of the inspiratory pressure sensor and the measured values of the expiratory pressure sensor.

8. A ventilator in accordance with claim 7, wherein the additional pressure sensor is arranged as a pressure sensor located close to the patient in the vicinity of the patient in or at the esophagus of the patient.

9. A ventilator in accordance with claim 1, wherein the control unit is configured to determine or to estimate the predefined values based on calculated or determined values, which indicate individual stiffnesses or elasticities of lungs, thorax and/or of a respiratory system of the patient.

10. A ventilator in accordance with claim 1, wherein the control unit is configured to determine or to estimate the predefined values based on an individually determined ratio of a stiffness or elasticity of lungs to a stiffness or elasticity of a respiratory system of the patient.

11. A ventilator in accordance with claim 10, wherein the control unit is configured to carry out the determination or estimation of the predefined values based on provided individual property data.

12. A ventilator in accordance with claim 10, wherein the control unit is configured to carry out the determination or estimation of the predefined values based on a determination of a difference of the end-expiratory lung volume of the patient at at least two different expiratory pressure levels.

13. A ventilator in accordance with claim 10, wherein the control unit is configured to carry out the determination or estimation of the predefined values based on a measurement maneuver with the use of an end-expiratory occlusion during the inhalation by the patient.

14. A ventilator in accordance with claim 10, wherein the control unit is configured to carry out the determination or estimation of the predefined values based on a measurement maneuver with the use of an end-expiratory occlusion during the exhalation by the patient.

15. A ventilator in accordance with claim 7, wherein the control unit is configured to take into account the measured value that indicates a pressure level inside the patient during the control of the inhalation valve, or of the exhalation valve or of the inhalation valve and of the exhalation valve.

16. A ventilator in accordance with claim 7, wherein the control unit is configured to take into account the measured value that indicates a pressure level inside the patient and a measured value that indicates an airway pressure inside the patient during the control of the inhalation valve or of the exhalation valve or of the inhalation valve and of the exhalation valve.

17. A system comprising:
a ventilator for a mechanical ventilation of a patient, the ventilator comprising: an exhalation valve; an inhalation valve; an inspiratory pressure sensor; an expiratory pressure sensor; a control unit; a ventilator data interface configured to provide predefined values to the control unit; and a connection system with an inhalation line for feeding breathing gases to the patient and with an exhalation line for removing breathing gases from the patient, wherein: the inspiratory pressure sensor is arranged in or at the inhalation line of the connection system; the inspiratory pressure sensor is configured to detect an inhalation pressure and to provide the inhalation pressure measured value for the control unit; the expiratory pressure sensor is configured to provide the expiratory pressure measured value for the control unit; the control unit is configured to control the inhalation valve taking into account the inhalation pressure measured value in order to provide an inspiratory pressure level via the inhalation line of the connection system for the patient; the control unit is configured to control the exhalation valve taking the expiratory pressure measured values into consideration in order to provide an expiratory pressure level for the patient via the exhalation line of the connection system; the control unit is configured to control the inhalation valve and the exhalation valve such as to raise the inspiratory pressure level from a first pressure level to a predefined second pressure level during an inspiration phase and to maintain the inspiratory pressure level for a first predefined time period during the inspiration phase; the control unit is configured to control the inhalation valve and the exhalation valve such as to raise the second pressure level to a predefined third pressure level during the inspiration phase and to maintain the third pressure level for a second predefined time period during the inspiration phase; and the control unit is configured to take predefined values into consideration during the control of the pressure levels and during the control of the time periods;
a measuring device arranged in or at the system or a measuring device associated with the system, wherein the measuring device is associated with a measuring device control unit for a measurement-based detection of a data set of invasive and/or non-invasive blood pressure measured values of the patient and for providing the data set of blood pressure measured values $P_{BP}$ by means of a measuring device data interface, wherein the ventilator data interface and the measuring device data interface are formed and intended for providing and implementing a wired and/or wireless communication with one another, and the communication between the ventilator and the measuring device provides for a coordinated operation of the measuring device and ventilator with a synchronization in time of the control of the inspiratory pressure level with the measurement-based detection of the data set of invasive and/or non-invasive blood pressure measured values.

18. A system in accordance with claim 17, wherein:
the communication is carried out unidirectionally or bidirectionally between the ventilator and the measuring device; and
the ventilator controls, during the coordinated operation, a maneuver with control of the pressure levels of the inspiratory pressure by the inhalation valve and with control of the expiratory pressure level by the exhalation valve and detection of the data set of invasive and/or non-invasive blood pressure measured values by the measuring device.

19. A system in accordance with claim 17, wherein:
the communication is carried out unidirectionally or bidirectionally between the ventilator and the measuring device; and
the measuring device controls, during the coordinated operation, a maneuver with control of the pressure levels of the inhalation pressure by the inhalation valve and with control of the pressure level of the exhalation valve by the ventilator and the detection of the data set of invasive and/or non-invasive blood pressure measured values.

20. A system in accordance with claim 17, wherein:
the communication is carried out unidirectionally or bidirectionally between the ventilator and the measuring device control unit as an external control unit or unidirectionally or bidirectionally between the measuring device and the measuring device control unit as an external control unit or unidirectionally or bidirectionally between the ventilator and the measuring device control unit as an external control unit and also unidirectionally or bidirectionally between the measuring device and the measuring device control unit as an external control unit; and
the external control unit controls, during the coordinated operation, a maneuver with control of the pressure levels by the ventilator comprising control of the inhalation pressure by the ventilator by control of the inhalation valve and control of the exhalation pressure by control of the exhalation valve by the ventilator.

21. A system in accordance with claim 17, wherein:
the communication is carried out unidirectionally or bidirectionally between the ventilator and the measuring device control unit as an external control unit or unidirectionally or bidirectionally between the measuring device and the external control unit or unidirectionally or bidirectionally between the ventilator and the measuring device control unit as an external control unit and also unidirectionally or bidirectionally between the measuring device and the external control unit; and
the external control unit controls, during the coordinated operation a maneuver with detection of the data set of invasive and/or non-invasive blood pressure measured values by the measuring device.

22. A system in accordance with claim 17, further comprising an analysis unit arranged in or at the system or an analysis unit associated with the system, wherein:
the analysis unit is configured to determine and to provide a slope value;
the determination of the slope value is carried out by forming a quotient of a difference of the blood pressure measured values detected during the maneuver and a difference of the pressure levels of the inhalation pressure which are set by the ventilator during the maneuver; and
a synchronization in time of the detected blood pressure measured values with the set pressure levels of the inhalation pressure is provided by the maneuver.

23. A system in accordance with claim 22, wherein the analysis unit uses arterial systolic blood pressure measured values from the data set of invasive and/or non-invasive blood pressure measured values to determine the slope value.

24. A system in accordance with claim 22, further comprising an output unit arranged in or at the system or an output unit associated with the system, wherein the output unit is configured to receive, to provide, to output or to display the slope value determined by the analysis unit.

* * * * *